(12) United States Patent
Kiersh et al.

(10) Patent No.: US 10,980,549 B2
(45) Date of Patent: Apr. 20, 2021

(54) GRAFT FILTER WITH LOCKING GRAFT FILTER ELEMENT AND GRAFT EXTRACTOR

(71) Applicant: DEPUY SYNTHES PRODUCTS, INC., Raynham, MA (US)

(72) Inventors: Jeff Kiersh, West Chester, PA (US); Michael Lehmicke, West Chester, PA (US); Christopher Shane, Strafford, PA (US); Ross Hamel, West Chester, PA (US); Dominic D'Andrea, Wallingford, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 322 days.

(21) Appl. No.: 15/896,450

(22) Filed: Feb. 14, 2018

(65) Prior Publication Data
US 2019/0247059 A1 Aug. 15, 2019

(51) Int. Cl.
| A61B 17/16 | (2006.01) |
| A61B 17/88 | (2006.01) |
| A61M 1/00 | (2006.01) |
| A61F 2/46 | (2006.01) |
| A61B 10/02 | (2006.01) |
| A61L 27/36 | (2006.01) |

(52) U.S. Cl.
CPC ...... *A61B 17/1635* (2013.01); *A61B 17/8833* (2013.01); *A61B 10/025* (2013.01); *A61B 2217/005* (2013.01); *A61B 2217/007* (2013.01); *A61F 2/4644* (2013.01); *A61F 2002/4645* (2013.01); *A61L 27/365* (2013.01); *A61M 1/0056* (2013.01)

(58) Field of Classification Search
CPC ............ A61B 17/1635; A61B 17/8833; A61B 2217/005; A61B 2217/007; A61B 10/025; A61M 1/0056; A61F 2/4644; A61F 2002/4645
USPC .......................................................... 606/80
See application file for complete search history.

(56) References Cited

U.S. PATENT DOCUMENTS

| 6,299,763 B1 | 10/2001 | Ashman |
| 6,332,886 B1 | 12/2001 | Green et al. |
| 6,387,070 B1 | 5/2002 | Marino et al. |
| 6,569,326 B1 | 5/2003 | Baumann et al. |
| 6,783,533 B2 | 8/2004 | Green et al. |

(Continued)

*Primary Examiner* — Marcela I. Shirsat
(74) *Attorney, Agent, or Firm* — Kramer Amado

(57) ABSTRACT

A device for collecting a bone graft material comprises a canister extending defining a filter-receiving space therein, the canister including a connection for connecting to a vacuum source, a proximal end of the canister including a first locking feature and a filter element sized and shaped to be received within the filter-receiving space of the canister, the filter element including a channel extending therethrough, the channel defined via a mesh material and a proximal end of the filter element including a second locking feature releasably engageable with the first locking feature of the canister via a rotation of the filter element about a longitudinal axis thereof relative to the canister in combination with an extractor sized and shaped to be received within the channel of the filter element, the extractor defining a graft material receiving space therein and being releasably engageable with the extractor.

17 Claims, 4 Drawing Sheets

(56) References Cited

U.S. PATENT DOCUMENTS

| | | | |
|---|---|---|---|
| 7,214,059 B2 * | 5/2007 | Takahashi | A61C 8/0089 |
| | | | 433/92 |
| 7,971,728 B2 | 7/2011 | Anspach et al. | |
| 8,088,189 B2 | 1/2012 | Matula et al. | |
| 8,308,835 B2 | 11/2012 | Dworatzek | |
| 8,622,953 B2 | 1/2014 | Hynes et al. | |
| 8,840,614 B2 | 9/2014 | Mikhail et al. | |
| 9,782,259 B2 | 10/2017 | Mikhail et al. | |
| D803,394 S | 11/2017 | Hamel et al. | |
| 2009/0306669 A1 * | 12/2009 | Takahashi | A61C 17/08 |
| | | | 606/80 |
| 2016/0184744 A1 * | 6/2016 | Jakop | B01D 46/0005 |
| | | | 417/313 |

* cited by examiner

GRAFT FILTER WITH LOCKING GRAFT FILTER ELEMENT AND GRAFT EXTRACTOR

BACKGROUND

Reamer Irrigator Aspirator (RIA) systems are used to ream and remove material from the medullary canals of bones such as, for example, the femur. Material from the medullary canal may be removed to prepare the bone for an intramedullary implant and/or to collect bone material for bone grafting treatments. An RIA system reams a bone while simultaneously providing irrigation and aspiration of the medullary canal. Irrigation reduces heat generated by the reamer device and emulsifies the reamed bone material. Aspiration removes the emulsified bone material from the medullary canal via a negative pressure applied through the MA system. A graft filter assembly collects the bone material and removes fluid from the emulsified bone material.

SUMMARY

The present embodiments are directed to a device for collecting a bone graft material comprising a canister extending longitudinally from a proximal end to a distal end and defining a filter-receiving space therein, the canister including a connection for connecting to a vacuum source, the proximal end of the canister including a first locking feature and a filter element sized and shaped to be received within the filter-receiving space of the canister, the filter element extending longitudinally from a proximal end to a distal end and including a channel extending therethrough, the channel defined via a mesh material and the proximal end of the filter element including a second locking feature releasably engageable with the first locking feature of the canister via a rotation of the filter element about a longitudinal axis thereof relative to the canister in combination with an extractor sized and shaped to be received within the channel of the filter element, the extractor defining a graft material receiving space therein and being releasably engageable with the extractor.

BRIEF DESCRIPTION

DETAILED DESCRIPTION

Figure 1:
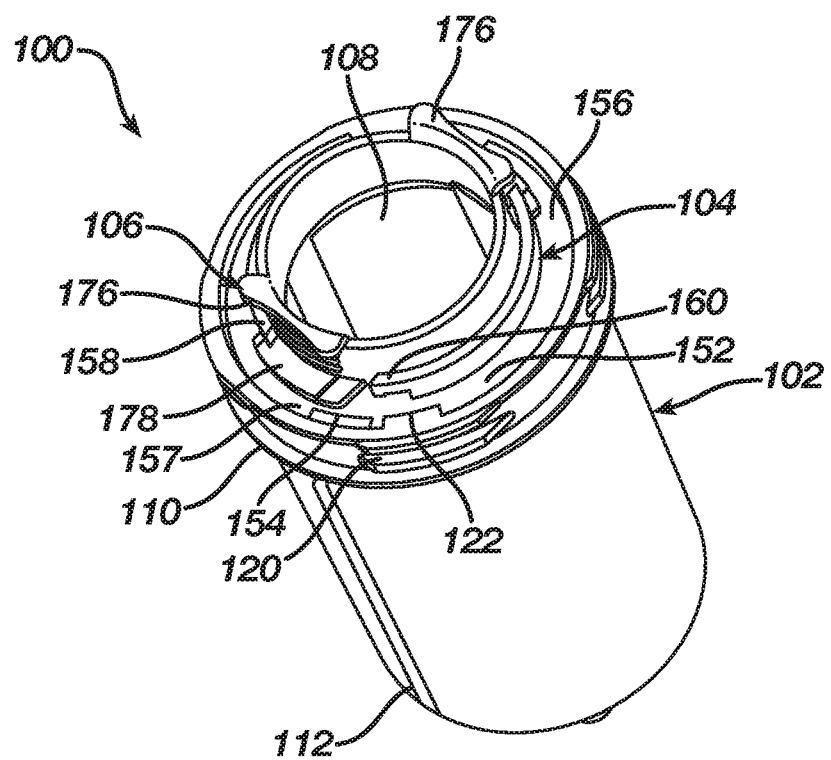
FIG. 1 shows a perspective view of a graft filter assembly according to an exemplary embodiment of the present disclosure.

The present disclosure may be further understood with reference to the following description and the appended drawings, wherein like elements are referred to with the same reference numerals. The present embodiments relate to the treatment of a bone and, in particular, relates the intramedullary reaming of a bone to remove bone material from the medullary canal of the bone. Material from the medullary canal may be collected for bone grafting. Exemplary embodiments describe a graft filter assembly which may be coupled to a reamer device to collect the reamed bone material as the material is being removed from the medullary canal via aspiration. The exemplary graft filter assembly includes a canister which receives a filter and an extractor. Each of these components—canister, filter and extractor—may be interlocked with one another to prevent the inadvertent disassembly thereof. It should be noted that the terms proximal and distal, as used herein, are intended to refer to a direction toward (proximal) and away from (distal) a user of the device.

As shown in FIGS. 1-5, a graft filter assembly 100 according to an exemplary embodiment of the present disclosure comprises a canister 102, a filter element 104 and an extractor 106 which releasably interlock with one another to prevent inadvertent disassembly thereof. The extractor 106 is sized and shaped to be received within the filter 104, which is sized and shaped to be received within the canister 102. The canister 102 houses the filter element 104 and the extractor 106 and is configured to be coupled to, for example, an aspiration port of a reamer device, which reams and removes material from a medullary canal of a long bone, and an aspiration hose for providing a suction force thereto. The reamer device may provide both irrigation and aspiration while the medullary canal is being reamed. During aspiration of the medullary canal, the reamed bone material, along with the fluid provided during irrigation, is suctioned through the aspiration port, to which the graft filter assembly 100 is connected, so that the reamed bone material is collected within a graft collecting space 108 of the extractor 106. As the graft material is received within the collecting space 108, fluid is filtered therefrom through a mesh material of the filter 104 and removed via the aspiration hose. Thus, only the desired graft material remains in the extractor 106 for removal upon completion of the reaming and collecting process.

Figure 2:
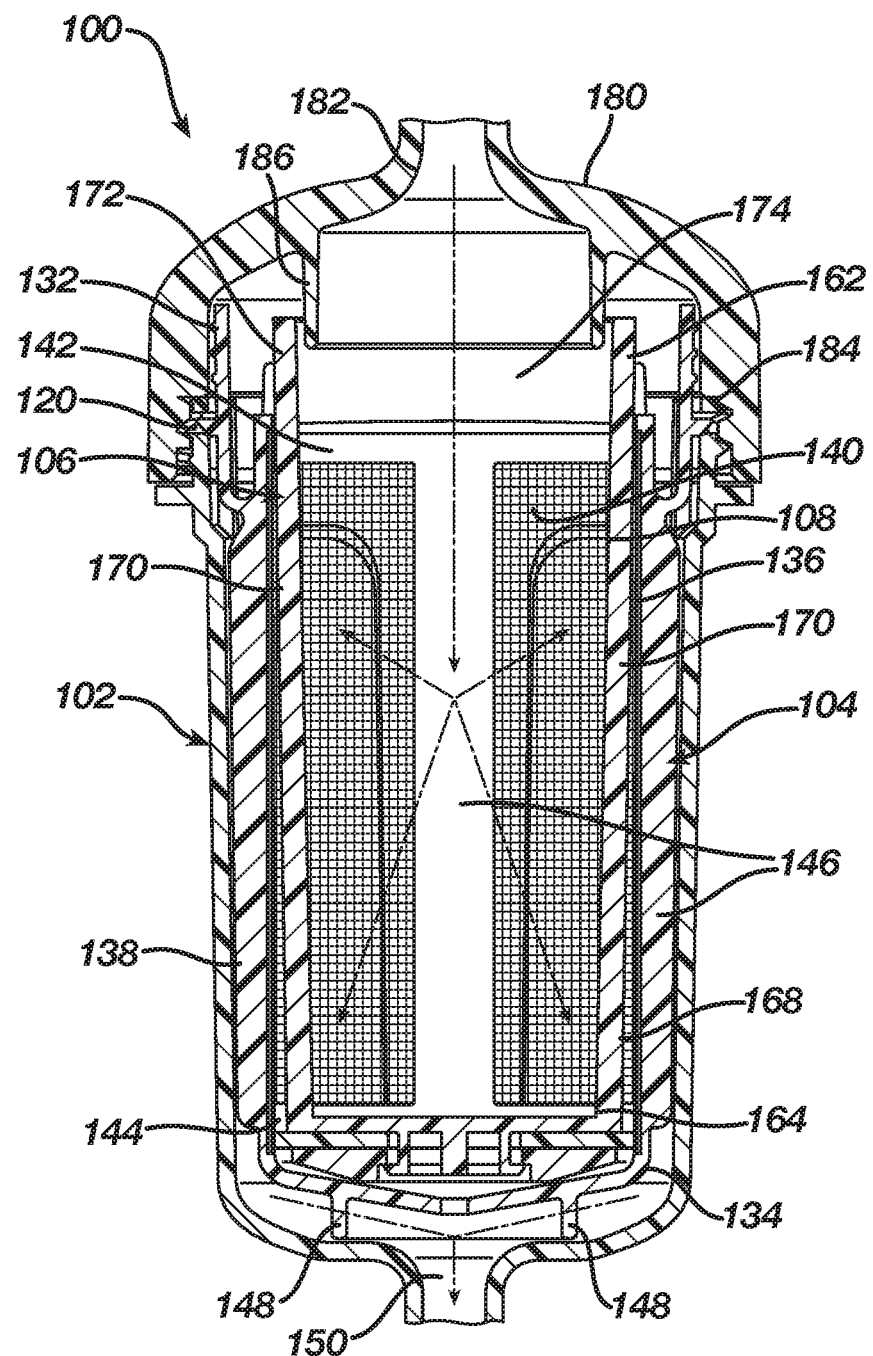
FIG. 2 shows a longitudinal cross-sectional view of a canister according to the graft filter assembly of FIG. 1.
Figure 3:
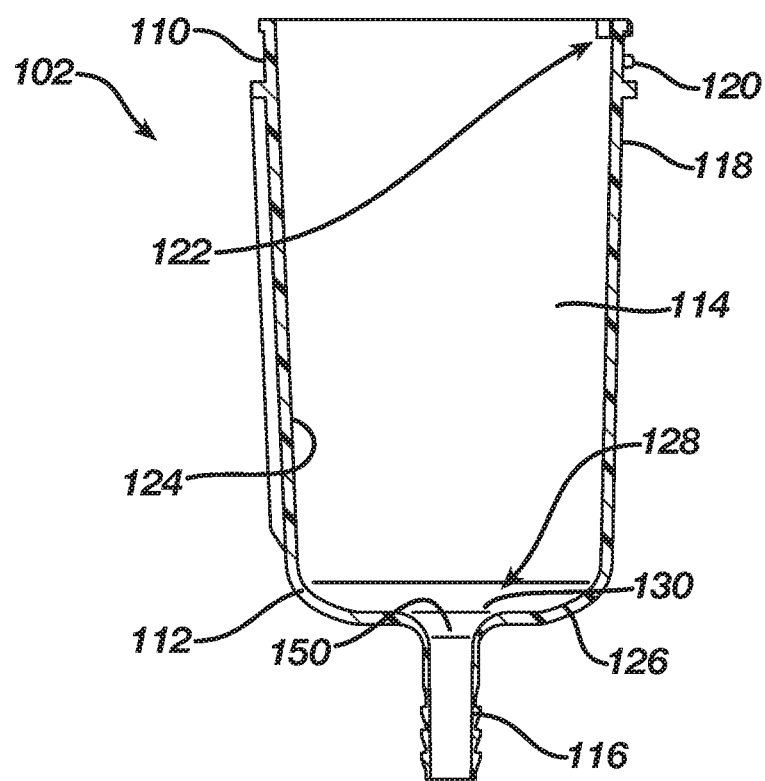
FIG. 3 shows a perspective view of a filter element and extractor according to the graft filter assembly of FIG. 1.
Figure 4:
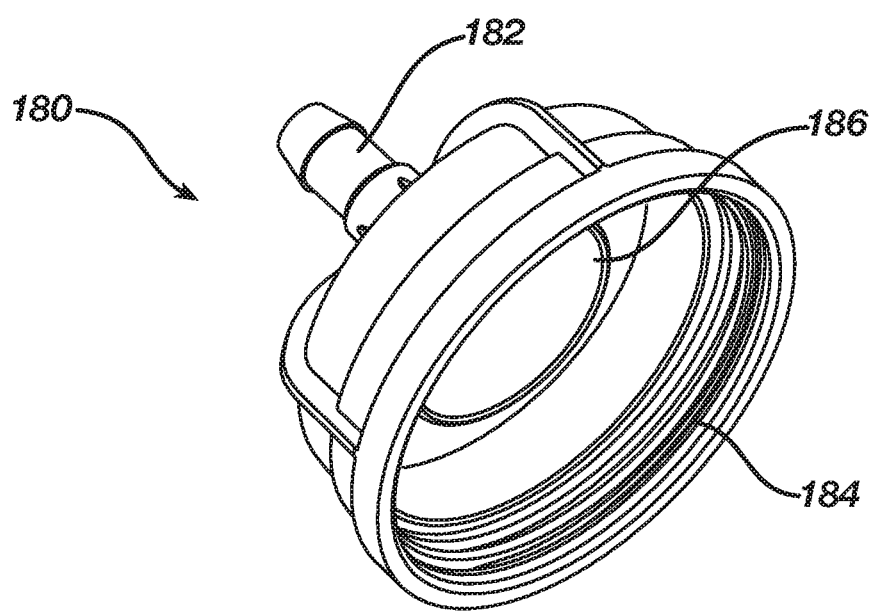
FIG. 4 shows a perspective view of the filter element according to FIG. 1.

As shown in FIGS. 1-3, the canister 102 extends longitudinally from a proximal end 110 to a distal end 112 and includes a channel 114 extending therethrough. The canister 102 according to this embodiment includes an open proximal end 110 so that the proximal end 110 may be connected to the reamer device via a lid 180, as shown in FIGS. 2 and 4, which is configured to be releasably coupled to the proximal end 110 of the canister 102. The lid 180 may be coupled to the proximal end 110 in any of a variety of ways. In one example, the first end 110 of the canister 102 includes threading 120 along an exterior surface 118 thereof for engaging corresponding threading 184 of the lid 180. As will be understood by those of skill in the art, the lid 180 may include a connector 182 for connecting to, for example, an aspiration port of the reamer device so that graft material may be drawn through the connector 182 of the lid 180 and into the channel 114 of the canister 102. The lid 180 may be particularly sized and shaped such that, when the lid 180 is connected to the canister 102 and a suction force is applied through the graft assembly 100, graft material is drawn into the collecting space 108 of the extractor 106, which is housed within the canister 102. For example, an interior of the lid 180 may include a structure 186 which, when the lid 180 is coupled to the canister 102, engages a proximal end 162 of the extractor 106 to direct suctioned graft material into the collecting space 108 of the extractor 106.

The first end 110 of the canister 102 according to this embodiment also includes a filter element retainer 122 configured as a planar protrusion extending radially into the channel 114 from an interior surface 124 of the channel 114. As will be described in further detail below, the filter element retainer 122 is configured to engage a proximal end 132 of the filter element 104 so that, when the filter element retainer 122 is in engagement with the filter element 104, the filter element 104 is prevented from being inadvertently disconnected therefrom.

The second end 112 of the canister 102 according to this embodiment includes a connector 116 for connecting to the aspiration hose. The connector 116 may include, for example, a barb connector for connecting to the aspiration hose. The connector 116 narrows an opening of the channel 114 at the distal end 112 so that all of the material suctioned from the channel 114 passes through the connector 116 into an aspiration hose connected thereto. In other words, a cross-sectional area of a portion of the channel 114 of this embodiment extending through the connector 116 is smaller than a cross-sectional area of a remaining portion of the channel 114. The canister 102 is thus shaped to include a shoulder 126 connecting the connector 116 to the remaining portion of the canister 102.

The canister 102 further includes a filter element ramp 128 along the interior surface 124 of the shoulder 126. The filter element ramp 128 includes a ramped surface 130 extending away from the interior surface 124 of the shoulder 126 toward the proximal end 110 to engage a distal end 134 of the filter element 104, as will be described in further detail below. The filter element ramp 126 of this embodiment extends along a portion of the shoulder 126 on the same side as the filter element retainer 122. In other words, the filter element ramp 126 and the filter element retainer 122 of this embodiment are substantially aligned along a plane extending longitudinally through a central axis of the canister 102. Although the filter element ramp 128 is described and shown as including the ramped surface 130, the filter element ramp 128 may be configured as a protrusion or any other projection which would provide a compressive force to the filter element 104, when the filter element 104 engages the filter element retainer 122. It will be understood by those of skill in the art that, when the filter element 104 and the canister 102 are engaged with one another, this compressive force prevents the filter element 104 from being inadvertently disengaged from the canister 102.

As shown in FIG. 2, the filter element 104 includes a mesh material 140 framed and held in a desired shape via a frame body 138. The frame body 138 extends longitudinally from the proximal end 132 to the distal end 134 and includes a channel 136 extending therethrough. The frame body 138 is sized and shaped to be received within the channel 114. In one embodiment, the frame body 138 may be defined via a first ring 142 at the proximal end 132 and a second ring 144 at the distal end 134, the first and second rings 142, 144 being connected to one another via a plurality of longitudinal struts 146. The mesh material 140 in this embodiment extends about an interior perimeter of the channel 136 of the filter element 104 so that mesh material 140 extends between adjacent ones of the plurality of longitudinal struts 146 to define a substantially cylindrical shape. The mesh material 140 extends about the interior of the longitudinal struts 146 so that, when the frame body 138 is received within the channel 114 of the canister 102, a space is formed between the mesh material 140 and an interior surface 124 of the channel 114. Thus, fluid may be filtered from the graft material collected within the mesh material via suctioning of the fluid into the space between mesh material 140 and the interior surface 124.

An opening at the proximal end 132 of the frame body 138 may be sized and shaped to permit the extractor 106 to be slidably received therein. An opening at the distal end 134 is smaller than the opening at the proximal end 132 so that the extractor 106, when received within the channel 136, is prevented from being moved distally past the distal end 134 of the filter element 104. The filter element 104 may further include a plurality of legs 148 extending distally from the distal end 134 so that, when the filter element 104 is received within the channel 114 of the canister 102, the distal end 134 is separated from the distal end 112 of the canister 102 to permit fluid filtered from the graft material to flow through an opening 150 of the connector 116 and into, for example, an aspiration hose connected thereto.

Figure 5:
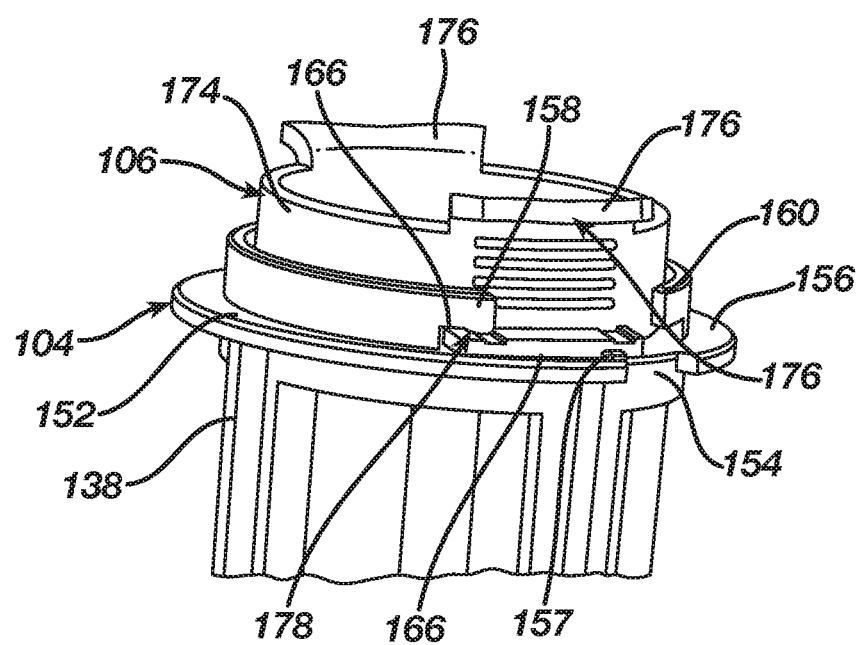
FIG. 5 shows a perspective view of the extractor according to FIG. 1.

As shown in FIG. 5, the frame body 138 according to this embodiment includes a lip 152 at the first end 132 configured to engage the first end 110 of the canister 102. In one embodiment, the lip 152 extends radially outward from the first end 132 and includes a groove 154 extending from a radially outermost edge of the lip 152 radially into the lip 152. The groove 154 is sized and shaped to permit the protrusion 122 of the canister 102 to pass therethrough. Thus, when the protrusion 122 and the groove 154 are aligned, the lip 152 is permitted to be moved distally there past so that, when rotated, the protrusion 122 engages a proximal surface 156 of the lip 152 along a portion of the lip 152 which does not include the groove 154.

Proximate the groove 154, along the proximal surface 156 of the lip 152, the filter element 104 may include a stop 157 protruding therefrom. The stop 157 prevents the protrusion 122 of the canister 102 from being aligned with the groove 154 upon continued rotation of the filter element 104 relative to the canister. In one embodiment, the stop 157 is proximate the groove 154, in a clockwise position relative to the groove 154 so that, when the lip 152 is permitted to move distally relative to the protrusion 122 and the filter element 104 is rotated clockwise relative to the canister 102, the protrusion 122 slides along the proximal surface 156 until the protrusion engages the stop 157. The stop 157 prevents a further clockwise rotation of the filter element 104 relative to the canister 102 so that the filter element 104 cannot be rotated a full 360 degrees and the filter element 104 is not inadvertently disengaged from the canister 102. In other words, the stop 157 prevents the groove 154 from being rotated into alignment with the protrusion 122 via the clockwise rotation of the filter element 104. Thus, when it is desired to disengage the filter element 104 from the canister 102, the filter element 104 may be rotated counter-clockwise relative to the canister 102 until the groove 154 is aligned with the protrusion 122. Although the stop 157 is shown and described as extending from the a portion of the lip 152 separated from the groove 154 in a clockwise direction, it will be understood by those of skill in the art that the stop 157 may be similarly positioned along the lip 152 counter-clockwise from the groove 154 so that the filter element 104 would be required to be rotated counter-clockwise relative to the canister 102 to lock the filter element 104 relative to the canister 102. As described above, when the filter element 104 is engaged with or locked relative to the canister 102, the filter element 104 is compressed between the protrusion 122 and the filter element ramp 126 so that the filter element 104 does not freely rotate relative to the canister 102 and inadvertently disengage therefrom. Rather, a force must be exerted on one of the canister 102 and the filter element 104 to cause relative rotation therebetween to disengage these elements from one another.

The first end 132 of the frame body 138 also includes a cut-out 166 defining a pair of hooks—a first hook 158 and a second hook 160. The cut-out 166 in this embodiment extends through the first ring 142 and is sized and shaped to permit a portion of the extractor 106 to be received therein and to selectively engage one of the first and second hooks 158, 160, depending on a direction of rotation of the extractor 106 relative to the filter element 104, as will be described in further detail below. In one embodiment, the frame body 138 includes a pair of cut-outs 156 diametrically opposed from one another, each defining the first and second hooks 158, 160.

The extractor 106, as shown in FIGS. 2 and 5, includes a body 168 extending longitudinally from a proximal end 162, through which graft material is collected therein, to a closed distal end 164 to define the bone graft collecting space 108 there within. The extractor 106 is sized and shaped to be received within the channel 136 of the filter element 104. The body 168 of the extractor 106 is structured so that, upon completion of the graft collection process, the extractor 106 may be removed from the filter element 104, and the collected graft material may be easily removed from the collecting space 108. For example, in one embodiment, the body 168 may be defined via at least two longitudinal struts 170 extending between the proximal and distal ends 162, 164. In one embodiment, proximal ends 172 of the longitudinal struts 170 may be connected to one another via a connecting ring 174. The body 168 of the extractor 106 is specifically structured so that fluid may be suctioned from the graft material collected within the collecting space 108 via the mesh material 140 of the filter element 104, which extends about the collecting space 108. In addition, upon removal of the extractor 106 from the filter element 104, the collected graft material is easily accessible from an exterior of the extractor 106 via between two adjacent struts 174.

The connecting ring 174 of the extractor 106 of this embodiment includes a pair of finger grips 176 diametrically opposed from one another and easily grippable by a user of the device. The connecting ring 174 may also include a detent 178 extending radially outward from the connecting ring 174, distally of the finger grips 176. The detent 178 is sized and shaped to be moved distally into the cut-out 166 as the extractor 106 is inserted into the channel 136 of the filter element 104. Once received within the cut-out 166, the extractor 106 may be rotated one of clockwise and counter-clockwise about a central axis thereof to engage one of the first and second hooks 158, 160, as desired. For example, when the extractor 106 is rotated clockwise, the detent 178 engages the first hook 158 and when the extractor 106 is rotated counter-clockwise, the detent 178 engages the second hook 160. When the detent 178 is engaged with one of the hooks 158, 160 of the filter element 104, the extractor 106 is locked relative to the filter element 104. When it is desired to disengage the extractor 106 from the filter element 104 to, for example, remove collected graft material, the user rotates the extractor 106 until the detent 178 does not engage either the first hook 158 or the second hook 160 and so that the detent 178 may be moved proximally out of the cut-out 166. In one embodiment, the extractor 106 includes a pair of detents 178. The detents 178 of this embodiment are diametrically opposed to one another and are positioned so that, for example, each detent 178 engages a corresponding one of the cut-outs 156 of the filter element 104.

Prior to use, the graft filter assembly 100 is assembled so that the assembled graft filter assembly 100 may be connected to, for example, a reamer device for the collection of graft material therein. As described above, the graft filter assembly 100 may be assembled by inserting the filter element 104 into the channel 114 of the canister 102 so that the groove 154 along the lip 152 of the filter element 104 is aligned with the protrusion 122 of the canister 102. The extractor 106 is inserted into the channel 136 of the filter element 104 so that the detent 178 of the extractor 106 is aligned with a corresponding cut-out 166 of the filter element 104. Using the finger grips 176, the user then moves the extractor 106 distally relative to the filter element 104 and rotates the extractor 106 in a first (e.g., clockwise) direction so that the detent 178 engages the first hook 158 of the cut-out 166. Once the detent 178 has engaged the first hook 158, continued rotation of the extractor 106 in the first direction causes the filter element 104 to also rotate in the first direction relative to the canister 102 so that the protrusion 122 of the canister 102 engages the proximal surface 156 of the lip 152 of the filter element 104. Thus, all three components—the canister 102, the filter element 104 and the extractor 106—are locked relative to one another and the assembly 100 is in the assembled configuration. Once the graft filter assembly 100 has been assembled, the lid is coupled to the proximal end 110 of the canister 102 via, for example, the threading 120. The graft filter assembly 100 may be then coupled to the reamer device via the lid and to an aspiration hose via the connector 116. As described above, the lid includes features for directing graft material into the collecting space 108 of the extractor 106.

In use, a vacuum force is applied through the aspiration hose so that reamed and/or irrigated bone material is suctioned from the bone material which the reamer device has drawn into the graft filter assembly 100. In particular, the bone material is directed into the collecting space 108 of the extractor 106 and fluid is suctioned therefrom through pores of the mesh material 140 of the filter element 104 and into the space between the mesh material 140 and the interior surface 124 of the channel 114 of the canister 102. The fluid is suctioned out of the canister 102 via the aspiration hose.

Upon completion of the reaming/collection process, the collected graft material may be removed from the graft filter assembly 100. According to one example, the extractor 106 may be rotated in the second (e.g., counter-clockwise) direction so that the detent 178 disengages the first hook 158 and engages the second hook 160. Once the detent 178 is engaged with the second hook 160, continued rotation of the extractor 106 in the second direction will also rotate the filter element 104 in the second direction. The extractor 106 and the filter element 104 may thus be rotated in the second direction until the groove 154 of the filter element 104 is aligned with the protrusion 122 of the canister 102. The extractor 106 and the filter element 104 may then be pulled proximally relative to the canister 102, removing the still-engaged extractor 106 and the filter element 104 from the canister 102. Once the extractor 106 and the filter element 104 have been removed from the canister 102, the extractor 106 may be disengaged from the filter element 104 by rotating the extractor 106 slightly, in the first direction, until the detent 178 disengages from the second hook 160 and can be pulled proximally out of the cut-out 166 by drawing the extractor 106 proximally out of the filter element 104. The graft material may then be removed from the collecting space 108 of the extractor 106. As described above, the graft material may be easily removed from the collecting space 108 since the collecting space 108 is substantially open to an exterior thereof.

According to another example, the graft material may be removed from the graft filter assembly 100 by disengaging only the extractor 106 from the filter element 104 and the canister 102. In this embodiment, the extractor 106 is simply rotated slightly in the second direction until the detent 178 disengages from the first hook 158 and the detent 178 may be removed from the cut-out 166 by drawing the extractor 106 proximally out of the channel 136 of the filter element 104. The graft material may then be removed from the collecting space 108 of the extractor 106.

As described above, the canister 102, the filter element 104 and the extractor 106 may be selectively and independently engaged and disengaged from one another so that the graft filter assembly 100 may be assembled and disassembled in a variety of configurations. Thus, it will be understood by those of skill in the art that the collected graft material may be removed from the graft filter assembly 100 by selectively disengaging the extractor 106 from the filter element 104 and/or the canister 102, as desired.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A device for collecting a bone graft material, comprising:
    a canister extending longitudinally from a proximal end to a distal end and defining a filter-receiving space therein, the canister including a connection for connecting to a vacuum source, the proximal end of the canister including a first locking feature;
    a filter element sized and shaped to be received within the filter-receiving space of the canister, the filter element extending longitudinally from a proximal end to a distal end and including a channel extending therethrough, the channel defined via a mesh material and the proximal end of the filter element including a second locking feature releasably engageable with the first locking feature of the canister via a rotation of the filter element about a longitudinal axis thereof relative to the canister; and
    an extractor sized and shaped to be received within the channel of the filter element, the extractor defining a graft material receiving space therein and being releasably engageable with the filter,
    wherein the filter element includes a third locking feature including a cut-out at a proximal end of the filter element, the cut-out defining a first hook and a second hook; and
    the extractor includes a fourth locking feature for releasably engaging the third locking feature of the filter element, the fourth locking feature including a detent extending radially outward from a proximal end of the extractor, the detent sized and shaped to be distally received within the cut-out so that a rotation of the extractor in a first direction about a longitudinal axis thereof relative to the filter causes the detent to engage the first hook and a rotation of the extractor in a second direction about the longitudinal axis relative to the filter element causes the detent to engage the second hook.

2. The device of claim 1, wherein the first locking feature includes a planar protrusion extending radially into the filter-receiving space of the canister.

3. The device of claim 1, wherein the filter element is sized and shaped so that, when the filter element is received within the filter-receiving space of the canister, a space is defined between an interior surface of the canister and an exterior surface of the filter element.

4. The device of claim 1, wherein proximally of the detent, the extractor includes a finger grip extending therefrom.

5. The device of claim 1, wherein the extractor is configured to be received within the channel of the filter element such that a distal end of the extractor is proximally distanced from the distal end of the filter element.

6. The device of claim 1, wherein the second locking feature includes a lip with a peripheral edge, the lip extends radially outward from the proximal end of the filter element, and a gap in the peripheral edge of the lip defines a groove extending radially inward from the peripheral edge of the lip.

7. The device of claim 6, wherein the groove in the peripheral edge of the lip is sired and shaped to correspond to the planar protrusion of the first locking feature so that, when the filter element is inserted into the filter-receiving space and the groove and protrusion are aligned with one another, the lip is movable distally past the protrusion such that rotation of the filter element in a first direction about a longitudinal axis thereof relative to the canister causes the protrusion to engage a proximal surface of the lip.

8. The device of claim 7, wherein the lip includes a stop extending from the proximal surface thereof proximate the groove to prevent the protrusion from becoming realigned with the groove during rotation of the filter element in the first direction.

9. A device for collecting a bone graft material, comprising
    a canister extending longitudinally from a proximal end to a distal end and defining a filter-receiving space therein, the canister including a connection for connecting to a vacuum source;
    a filter element sized and shaped to be received within the filter-receiving space of the canister, the filter element extending longitudinally from a proximal end to a distal end and including a channel extending therethrough, the channel defined via a mesh material and the proximal end of the filter element being releasably engageable with the canister; and
    an extractor sized and shaped to be received within the channel of the filter element, the extractor defining a graft material receiving space therein and being releasably engageable with the filter,
    wherein the filter element includes a cut-out at a proximal end of the filter element, the cut-out defining a first hook and a second hook, the first and second hooks facing opposite directions; and
    the extractor includes a detent extending radially outward from a proximal end of the extractor, the detent adapted to be distally received within the cut-out so that a rotation of the extractor in a first direction about a longitudinal axis thereof relative to the filter causes the detent to engage the first hook and a rotation of the extractor in a second direction about the longitudinal axis relative to the filter element causes the detent to engage the second hook.

10. The device of claim 9, wherein
    the proximal end of the canister includes a first locking feature; and
    the proximal end of the filter element includes a second locking feature configured to releasably engage the first locking feature of the canister via a rotation of the filter element about a longitudinal axis thereof relative to the canister.

11. The device of claim 10, wherein the first locking feature includes a planar protrusion extending radially into the filter-receiving space of the canister.

12. The device of claim 10, wherein the second locking feature includes a lip with a peripheral edge, the lip extends radially outward from the proximal end of the filter element, and a gap in the peripheral edge of the lip defines a groove extending radially inward from the peripheral edge of the lip.

13. The device of claim 12, wherein the groove in the peripheral edge of the lip is sized and shaped to correspond to the planar protrusion of the first locking feature so that, when the filter element is inserted into the filter-receiving space and the groove and protrusion are aligned with one another, the lip is movable distally past the protrusion such that rotation of the filter element in a first direction about a longitudinal axis thereof relative to the canister causes the protrusion to engage a proximal surface of the lip.

14. The device of claim 13, wherein the lip includes a stop extending from the proximal surface thereof proximate the groove to prevent the protrusion from becoming realigned with the groove during rotation of the filter element in the first direction.

15. The device of claim 9, wherein the filter element is sized and shaped so that, when the filter element is received within the filter-receiving space of the canister, a space is defined between an interior surface of the canister and an exterior surface of the filter element.

16. The device of claim 9, wherein proximally of the decent, the extractor includes a finger grip extending therefrom.

17. The device of claim 9, wherein the extractor is configured to be received within the channel of the filter element such that a distal end of the extractor is proximally distanced from the distal end of the filter element.

\* \* \* \* \*